(12) United States Patent
Leemrijse et al.

(10) Patent No.: US 12,721,632 B2
(45) Date of Patent: Sep. 1, 2026

(54) PATIENT-SPECIFIC INSTRUMENTS FOR PERFORMING BONE CUTS

(71) Applicant: In2Bones SAS, Ecully (FR)

(72) Inventors: Thibaut Jean Pierre Henry Leemrijse, Ecully (FR); Pit Putzeys, Ecully (FR); Laurent Francois Rene Paul, Ecully (FR); Per-Henrik Agren, Ecully (FR); Jean-Luc Pierre Marie Besse, Ecully (FR)

(73) Assignee: In2Bones SAS, Ecully (FR)

( * ) Notice: Subject to any disclaimer, the term of this patent is extended or adjusted under 35 U.S.C. 154(b) by 10 days.

(21) Appl. No.: 16/768,540

(22) PCT Filed: May 28, 2020

(86) PCT No.: PCT/EP2020/064840
§ 371 (c)(1),
(2) Date: May 29, 2020

(87) PCT Pub. No.: WO2020/239909
PCT Pub. Date: Dec. 3, 2020

(65) Prior Publication Data

US 2022/0346806 A1 Nov. 3, 2022

Related U.S. Application Data

(60) Provisional application No. 62/853,389, filed on May 28, 2019.

(51) Int. Cl.

| | |
|---|---|
| ***A61B 17/15*** | (2006.01) |
| ***A61B 17/17*** | (2006.01) |
| *A61B 17/56* | (2006.01) |

(52) U.S. Cl.
CPC ........ *A61B 17/151* (2013.01); *A61B 17/1775* (2016.11); *A61B 2017/568* (2013.01)

(58) Field of Classification Search
CPC ....... A61B 17/15; A61B 17/151; A61B 17/17; A61B 17/1775; A61B 17/56
See application file for complete search history.

(56) References Cited

U.S. PATENT DOCUMENTS

| | | | | |
|---|---|---|---|---|
| 9,017,334 B2 * | 4/2015 | Carroll | A61B 34/10 606/86 R |
| 2010/0217338 A1 * | 8/2010 | Carroll | A61B 34/10 606/86 R |

(Continued)

FOREIGN PATENT DOCUMENTS

| | | |
|---|---|---|
| WO | WO-2011/106409 | 9/2011 |
| WO | WO-2019/091537 | 5/2019 |

*Primary Examiner* — Christopher J Beccia
(74) *Attorney, Agent, or Firm* — Rutan & Tucker LLP; Hani Z. Sayed

(57) ABSTRACT

An apparatus and a method are provided for a patient-specific instrument guide for arthroplasty or other operations on bone tissue, capable of limiting bone cuts, achieving optimal implant positioning, and providing improved stability of implants. The patient-specific instrument guide comprises a body that includes a bone contact surface configured to contact a bone surface of a patient. The body is configured to be 3D printed according to medical imaging of a patient's anatomy, such that the bone contact surface optimally contacts the surface of the patient's bone. The body includes one or more guide slots that each slidably receives a cutting guide. The cutting guides are configured to receive a saw blade during bone cutting. The cutting guides may be oriented to guide cutting a talus or a tibia during a total ankle arthroplasty surgery.

18 Claims, 13 Drawing Sheets

(56) References Cited

U.S. PATENT DOCUMENTS

| | | | | |
|---|---|---|---|---|
| 2013/0150862 | A1* | 6/2013 | Aram | A61B 17/1764 606/88 |
| 2014/0343403 | A1 | 11/2014 | Kunz et al. | |
| 2015/0182273 | A1* | 7/2015 | Stemniski | A61B 17/1739 606/96 |
| 2018/0185097 | A1 | 7/2018 | Langhorn et al. | |
| 2019/0015119 | A1* | 1/2019 | Athwal | A61B 17/1684 |
| 2020/0138491 | A1* | 5/2020 | Brigido | A61B 17/84 |
| 2020/0367910 | A1* | 11/2020 | Hafez | A61B 17/15 |

* cited by examiner

PATIENT-SPECIFIC INSTRUMENTS FOR PERFORMING BONE CUTS

PRIORITY

This application claims the benefit of and priority to PCT Application No. PCT/EP2020/064840 filed on May 28, 2020 and U.S. Provisional Application, entitled "Patient-Specific Instrument For Performing Bone Cuts," filed on May 28, 2019 and having application Ser. No. 62/853,389, the entirety of said application being incorporated herein by reference.

FIELD

Embodiments of the present disclosure generally relate to the field of surgical implants. More specifically, embodiments of the disclosure relate to patient-specific instruments for arthroplasty or other operations on bone tissue, capable of limiting bone cuts, achieving optimal implant positioning, and providing improved stability of implants.

BACKGROUND

Arthroplasty, also known as joint replacement, is a surgical procedure whereby end-stage arthritis is treated. Arthritic changes may be a result of normal wear and tear due to aging or due to an injury such as a fracture or dislocation. Arthritis eventually leads to a loss of cartilage, pain, and/or deformity. Arthroplasty generally involves resurfacing the ends of articulating bones with metal implants and placing a plastic piece therebetween. Similar procedures are involved in total ankle, total knee and hip, and other joint replacement surgeries. Osteotomy is a surgical procedure aiming at cutting the geometry of a bone to correct deformities originating from congenital malformations, bone growth diseases, sequelae form injuries or bone fractures.

Potential complications associated with total arthroplasty include risks generally associated with surgery such as anesthesia, infection, damage to nerves and blood vessels, and bleeding or blood clots. Fracture of bone near the metal implants is the most common complication associated with arthroplasty. In some instances, injury to tendons, nerves, or blood vessels may be a possible complication of joint replacement. Further, another complication that sometimes occurs is the failure of the metal implants to heal into the bone. As such, there is a continuing desire to develop surgical instruments and implants that minimize or eliminate the complications associated with total ankle replacements. Potential complications of osteotomies include residual deformities or delayed consolidations of bones resulting from inaccurate bone cuts.

Embodiments presented herein are directed to patient-specific instruments for total arthroplasty or osteotomies capable of limiting bone cuts, achieving optimal implant positioning, and providing improved stability of implants.

SUMMARY

An apparatus and a method are provided for a patient-specific instrument guide for arthroplasty or other operations on bone tissue, capable of limiting bone cuts, achieving optimal implant positioning, and providing improved stability of implants. The patient-specific instrument guide comprises a body that includes a bone contact surface configured to contact a bone surface of a patient. The body is configured to be 3D printed according to medical imaging of a patient's anatomy, such that the bone contact surface optimally contacts the surface of the patient's bone. The body includes one or more guide slots that each slidably receives a cutting guide. The cutting guides are configured to receive a saw blade during bone cutting. The cutting guides may be oriented to guide cutting a talus or a tibia during a total ankle arthroplasty surgery.

In an exemplary embodiment, a patient-specific instrument guide comprises: a body comprising a bone contact surface configured to contact a bone surface of a patient; and one or more cutting guides configured to receive a saw blade during cutting the bone.

In another exemplary embodiment, the one or more cutting guides are comprised of a metal suitable for protecting the body from a saw blade during bone cutting. In another exemplary embodiment, the one or more cutting guides each includes a saw blade slot configured to guide a saw blade during bone cutting.

In another exemplary embodiment, the body includes one or more guide slots that each slidably receives one of the one or more cutting guides. In another exemplary embodiment, the one or more cutting guides comprises a horizontal cutting guide and a vertical cutting guide orientated to guide cutting a talus during a total ankle arthroplasty surgery. In another exemplary embodiment, the one or more cutting guides comprises a horizontal cutting guide oriented to guide cutting a tibia during a total ankle arthroplasty surgery.

In another exemplary embodiment, the body is comprised of a 3D printable material. In another exemplary embodiment, the body is configured to be 3D printed according to medical imaging of a patient's anatomy. In another exemplary embodiment, the bone contact surface is configured to optimally contact the surface of a specific bone of the patient. In another exemplary embodiment, the specific bone is a tibia for the purpose of a total ankle arthroplasty surgery. In another exemplary embodiment, the specific bone is a talus for the purpose of a total ankle arthroplasty surgery.

In another exemplary embodiment, one or more fixation holes are disposed at the front of the body and extend to the bone contact surface. In another exemplary embodiment, the one or more fixation holes are configured to received fixation pins to hold the bone contact surface in direct contact with the bone.

In another exemplary embodiment, the cutting guide includes at least one angulated pin slot that extends from the front to the back of the cutting guide. In another exemplary embodiment, the at least one angulated pin slot is configured to fixate the cutting guide within the body. In another exemplary embodiment, one or more positioning holes are disposed along a top of the body and configured to receive positioning pins to assist a surgeon with optimally positioning the bone contact surface with the bone.

In another exemplary embodiment, the body includes one or more angled implant positioning holes that are configured to receive positioning pins. In another exemplary embodiment, the one or more angled implant positioning holes are configured to assist a surgeon with preparing properly angled holes to receive pegs of an implant. In another exemplary embodiment, the one or more angled implant positioning holes are configured to guide a surgeon with driving positioning pins into a bone at an optimal angle and separation distance, the positioning pins being configured to receive a cannulated drill for the purpose of drilling holes in the bone in preparation for coupling the implant to the bone.

In an exemplary embodiment, a patient-specific instrument guide comprises: a body comprising a bone contact surface configured to contact a bone surface of a patient, wherein the body includes a multiplicity of angled holes extending through the body in parallel so as to provide visibility of the bone surface underneath the body so as to optimize a surgeon's view of the bone surface during cutting of the bone. In another exemplary embodiment, each of the multiplicity of angled holes comprises a cross-sectional shape capable of tessellating the surface of the body.

BRIEF DESCRIPTION OF THE DRAWINGS

The drawings refer to embodiments of the present disclosure in which.

Figure 1:
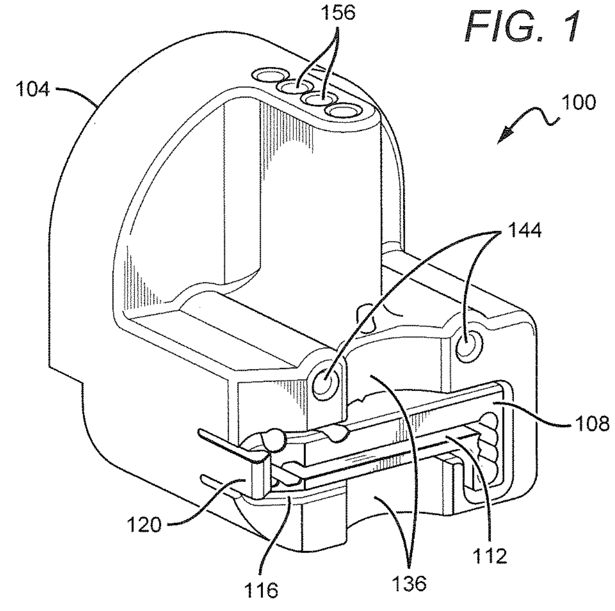
FIG. 1 illustrates an isometric view of an exemplary embodiment of a patient-specific instrument guide that is configured to guide cuts to a tibia during performing a total ankle arthroplasty surgery.

While the present disclosure is subject to various modifications and alternative forms, specific embodiments thereof have been shown by way of example in the drawings and will herein be described in detail. The invention should be understood to not be limited to the particular forms disclosed, but on the contrary, the intention is to cover all modifications, equivalents, and alternatives falling within the spirit and scope of the present disclosure.

DETAILED DESCRIPTION

In the following description, numerous specific details are set forth in order to provide a thorough understanding of the present disclosure. It will be apparent, however, to one of ordinary skill in the art that the invention disclosed herein may be practiced without these specific details. In other instances, specific numeric references such as "first implant," may be made. However, the specific numeric reference should not be interpreted as a literal sequential order but rather interpreted that the "first implant" is different than a "second implant." Thus, the specific details set forth are merely exemplary. The specific details may be varied from and still be contemplated to be within the spirit and scope of the present disclosure. The term "coupled" is defined as meaning connected either directly to the component or indirectly to the component through another component. Further, as used herein, the terms "about," "approximately," or "substantially" for any numerical values or ranges indicate a suitable dimensional tolerance that allows the part or collection of components to function for its intended purpose as described herein.

A total ankle arthroplasty may be performed to treat end-stage ankle arthritis due to normal wear and tear due to aging or due to an injury such as a broken ankle or dislocation. Complications associated with total ankle arthroplasty include risks generally associated with surgery, as well as potential fracturing of bone near metal implants associated with total ankle arthroplasty. In some instances, injury to tendons, nerves, or blood vessels, or a failure of the metal implants to heal into the bone may be possible complications of total ankle arthroplasty. Embodiments presented herein are directed to patient-specific instruments for total ankle arthroplasty that overcome the foregoing complication and are capable of limiting bone cuts, achieving optimal implant positioning, and providing improved stability of implants.

Figure 2:
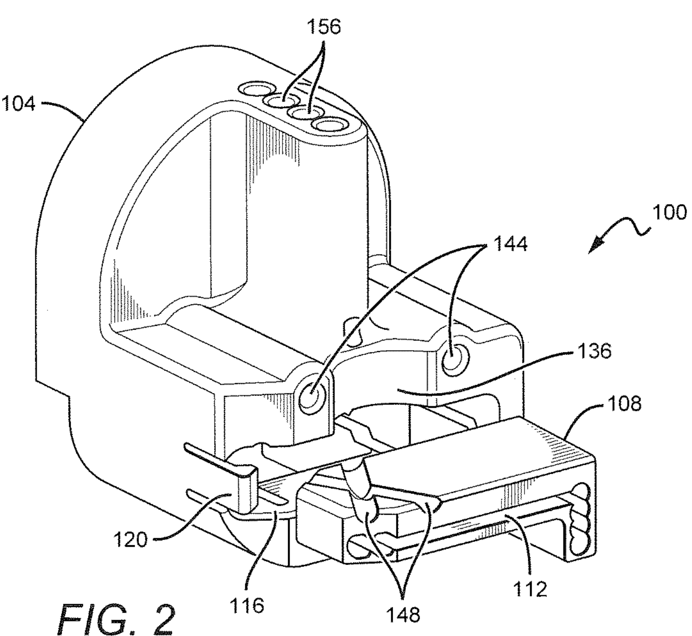
FIG. 2 illustrates an exploded isometric view of an exemplary embodiment of a patient-specific instrument guide that is configured to performing total ankle arthroplasty surgeries.

FIGS. 1-2 illustrate isometric views of an exemplary embodiment of a patient-specific instrument guide 100 (hereinafter, "PSI guide 100") that is configured to performing total ankle arthroplasty surgeries. The PSI guide 100 includes a bone contact surface 104, a cutting guide 108, and a saw blade slot 112 disposed in the cutting guide 108. As best shown in FIG. 2, the PSI guide 100 generally comprises a monolithic body that includes a guide slot 116 that slidably receives the cutting guide 108. It is contemplated that the PSI guide 100 is comprised of a rigid material, such as a 3D printable material, that may be adapted to a specific bone surface of a patient. The cutting guide 108 preferably is comprised of a metal suitable for protecting the PSI guide 100 from a saw blade during bone cutting. As will be appreciated, although the PSI guide 100 is intended to be patient-specific, the cutting guide 108 generally is reusable.

It should be borne in mind that although saw blade slots are discussed herein and illustrated in the drawings, the PSI guide is not limited to saw blade slots. Rather, it is contemplated that, in some embodiments, the PSI guide 100 may be adapted for use with bone cutting instruments other than saw blades, such as, by way of non-limiting example, any of various suitable bone drills and reamers. As such, it should be understood that in such embodiments, the saw blade slot 112 may be adapted to guide bone drills and/or reamers to specific bone surfaces of a patient, as desired, and without limitation.

Figure 3:
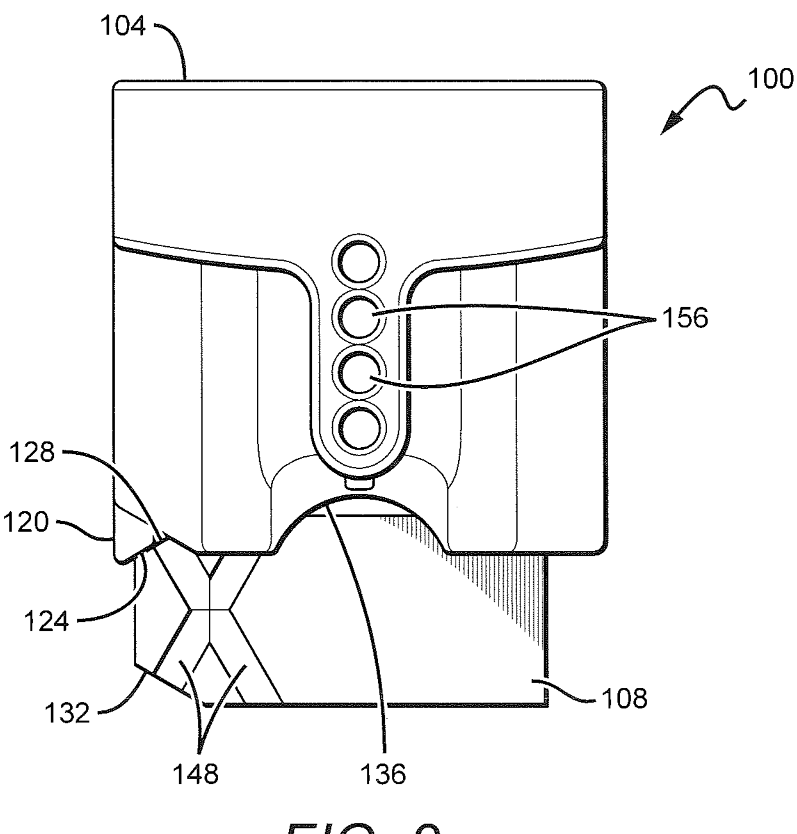
FIG. 3 illustrates a top view of the patient-specific instrument guide of FIG. 2.
Figure 4:
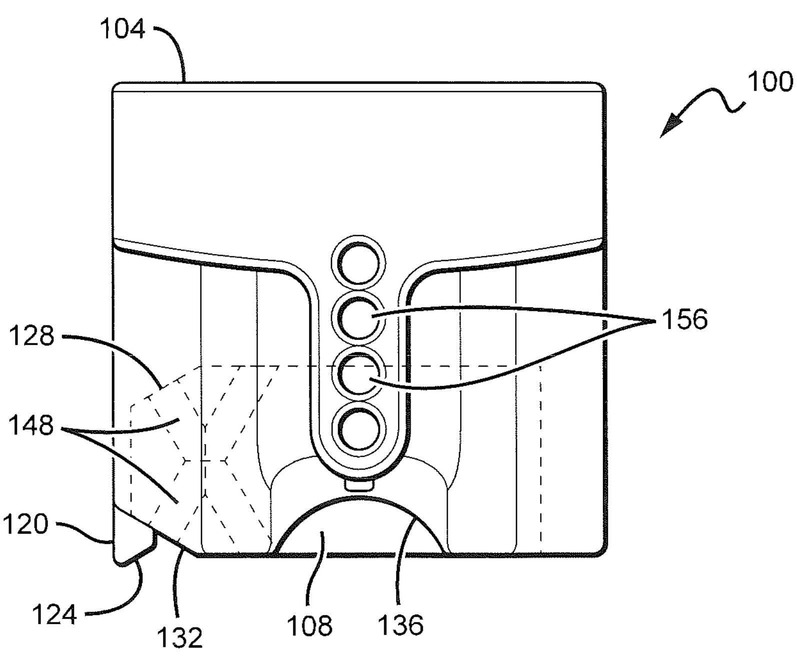
FIG. 4 illustrates a top ghost view of the patient-specific instrument guide of FIG. 1.

The PSI guide 100 includes a retaining arm 120 that is disposed adjacent to the guide slot 116 and configured to hold the cutting guide 108 within the guide slot 116. As best shown in FIGS. 3-4, the retaining arm 120 includes a distal protrusion 124 configured to slidably engage with chamfered surfaces 128, 132 of the cutting guide 108. Specifically, upon a practitioner inserting the cutting guide 108 into the guide slot 116, the chamfered surface 128 pushes on the distal protrusion 124, flexing the retaining arm 120 outwards, and thereby causing the distal protrusion 124 to be passed around the side of the cutting guide 108. The distal protrusion 124 engages with the chamfered surface 132 once the cutting guide 108 is optimally inserted into the guide slot 116, as shown in FIG. 4.

Figure 5:
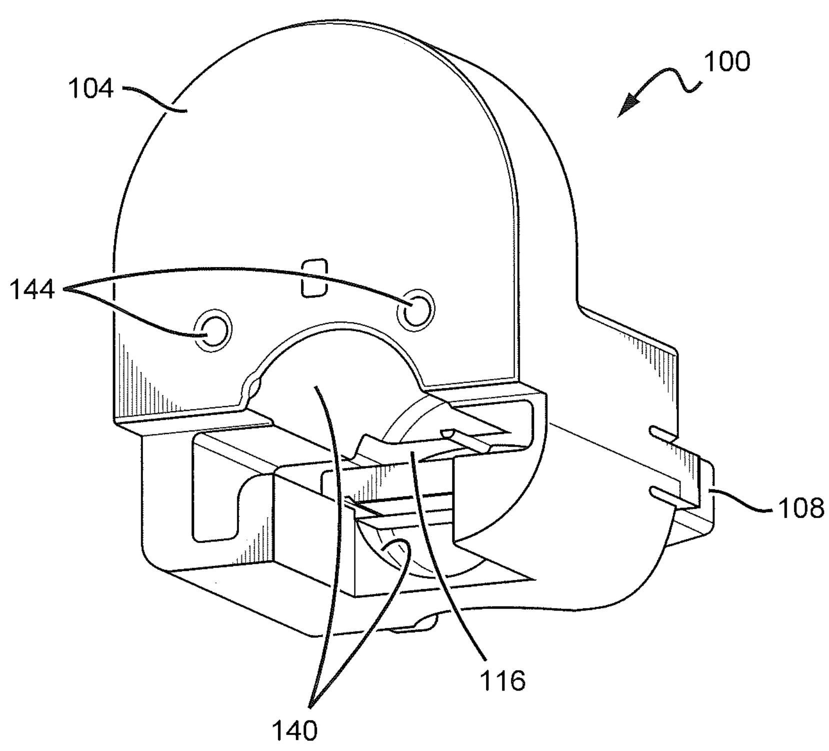
FIG. 5 illustrates an isometric view of a bone contact surface before personalization of the patient-specific instrument guide of FIG. 2.
Figure 6:
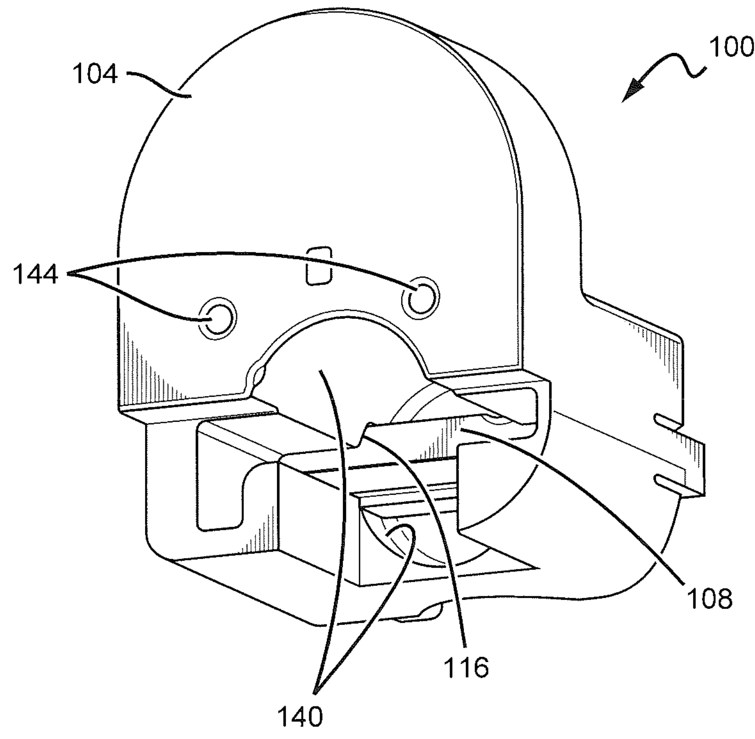
FIG. 6 illustrates an isometric view of a bone contact surface before personalization of the patient-specific instrument guide of FIG. 1.

As will be appreciated, the engagement of the distal protrusion 124 with the chamfered surface 132 retains the cutting guide 108 within the guide slot 116 until the practitioner pulls the cutting guide 108 loose from the PSI guide 100. As shown in FIGS. 1-4, the PSI guide 100 includes a front notch 136 disposed above and below the cutting guide 108 to enable the practitioner to grasp the cutting guide 108 with an index finger and a thumb. Further, as shown in FIGS. 5-6, the PSI guide 100 includes a rear notch 140 behind the cutting guide 108, disposed above and below the guide slot 116. It is contemplated that the rear notches 140 enable the practitioner to use a finger or a thumb to push the cutting guide 108 out of the guide slot 116.

Figures 7, 8:
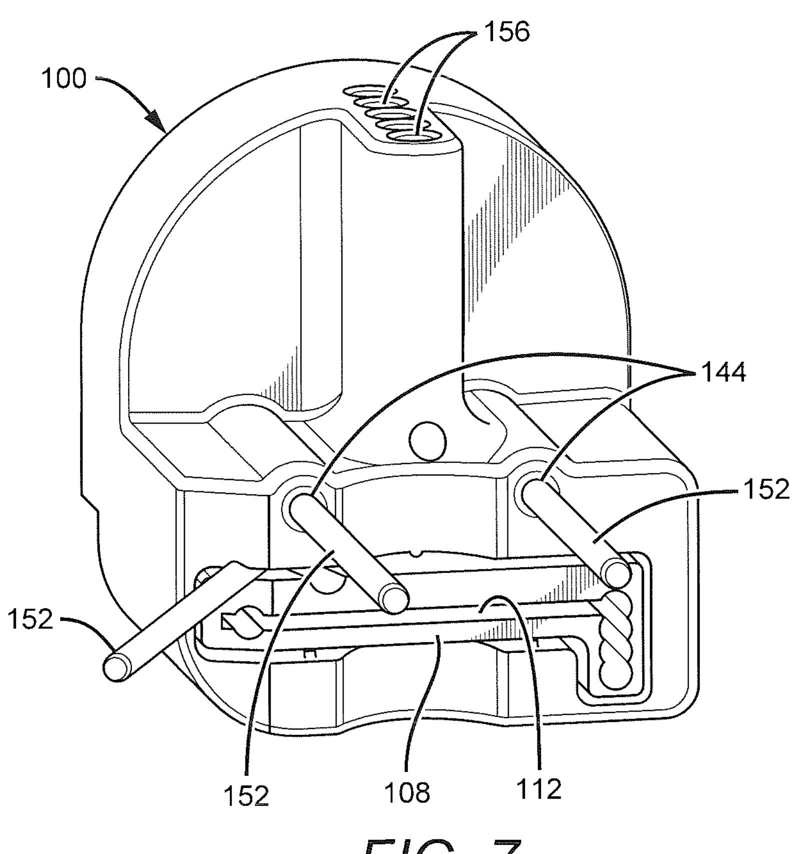
FIG. 7 illustrates an isometric view of an exemplary embodiment of a patient-specific instrument guide including fixation pins.
FIG. 8 illustrates an isometric view of an exemplary embodiment of a patient-specific instrument guide that is coupled with a tibia.

Referring again to FIGS. 1-2, the PSI guide 100 includes several holes to enable to the PSI guide 100 to be optimally fixated to a target bone of a patient to be treated. A pair of fixation holes 144 are disposed at the front of the PSI guide 100 and extend through the guide 100 to the bone contact surface 104, as shown in FIGS. 5-6. Further, as best shown in FIGS. 2-3, the cutting guide 108 includes at least one angulated pin slot 148 that extends from the front to the back of the cutting guide 108. The fixation holes 144 and the angulated pin slot 148 are configured to receive fixation pins 152, as shown in FIG. 7. The fixation pins 152 extending through the fixation holes 144 hold the bone contact surface 104 in direct contact with a target bone to be treated, such as a tibia 154 as shown in FIG. 8. The fixation pin 152 extending through the angulated pin slot 148 is configured to fixate the cutting guide 108 within the guide slot 116. Further, multiple positioning holes 156 are disposed along a top of the PSI guide 100, as shown in FIGS. 1-4. It is contemplated that the positioning holes 156 are particularly suitable for receiving one or more positioning pins 160, as shown in FIG. 8, to assist a surgeon with optimally positioning the PSI guide 100 in contact with a target bone, such as the tibia 154.

Figures 9, 10, 11:
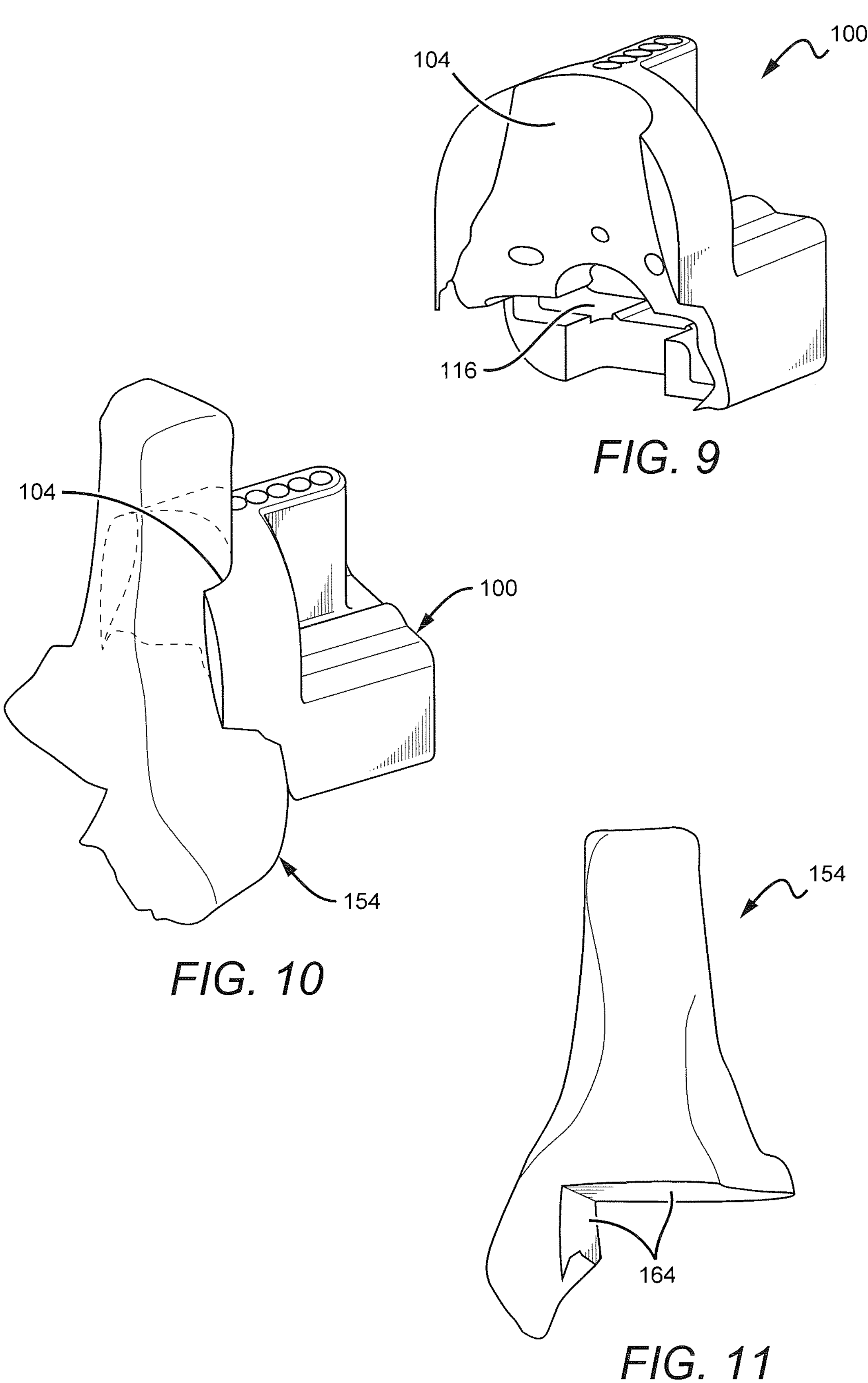
FIG. 9 illustrates an isometric view of an exemplary embodiment of a patient-specific instrument guide that includes a bone contact surface adapted to a specific bone of a patient.
FIG. 10 illustrates the patient-specific instrument guide of FIG. 9 optimally coupled with a tibia.
FIG. 11 illustrates bone cuts applied to the tibia of FIG. 10 after the patient-specific instrument guide of FIG. 9 is removed from the tibia.

As mentioned hereinabove, the PSI guide 100 is contemplated to be capable of being adapted to a specific bone surface of a patient, such as the tibia 154 shown in FIG. 8. FIGS. 5-6 illustrate the bone contact surface 104 before being personalized to a bone surface of a patient, whereas FIG. 9 illustrates an exemplary embodiment of the bone contact surface 104 that has been adapted to contact the tibia 154 of the patient, as shown in FIG. 10. It is envisioned that the bone contact surface 104 can be adapted to the target bone surface, such as the tibia 154, based on medical imaging. As such, the PSI guide 100 and the bone contact surface 104 may be 3D printed according to the patient's anatomy, allowing for precise positioning of the PSI guide 100 in preparation for performing a precise bone cut. For example, during a total ankle arthroplasty, the PSI guide 100 is placed in optimal contact with the target bone, such as the tibia 154 shown in FIG. 10, a saw blade is inserted through the saw blade slot 112, discussed with respect to FIGS. 1-2, and precise bone cuts 164 are formed in the tibia 154, as shown in FIG. 11.

Figure 12:
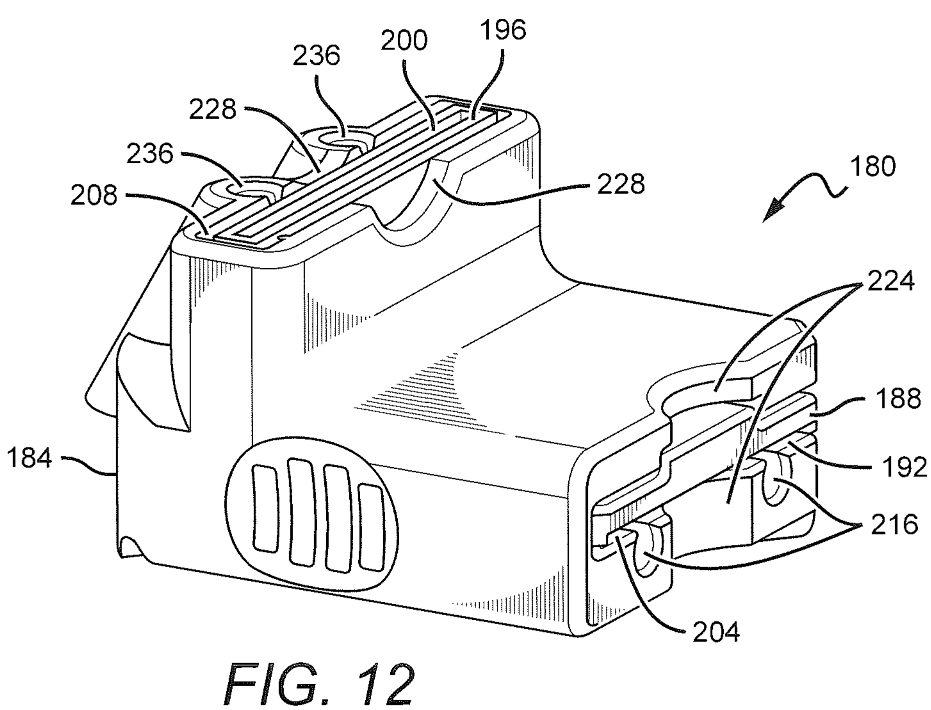
FIG. 12 illustrates an isometric view of an exemplary embodiment of a patient-specific instrument guide that is configured to guide cuts to a talus during performing a total ankle arthroplasty surgery.
Figure 13:
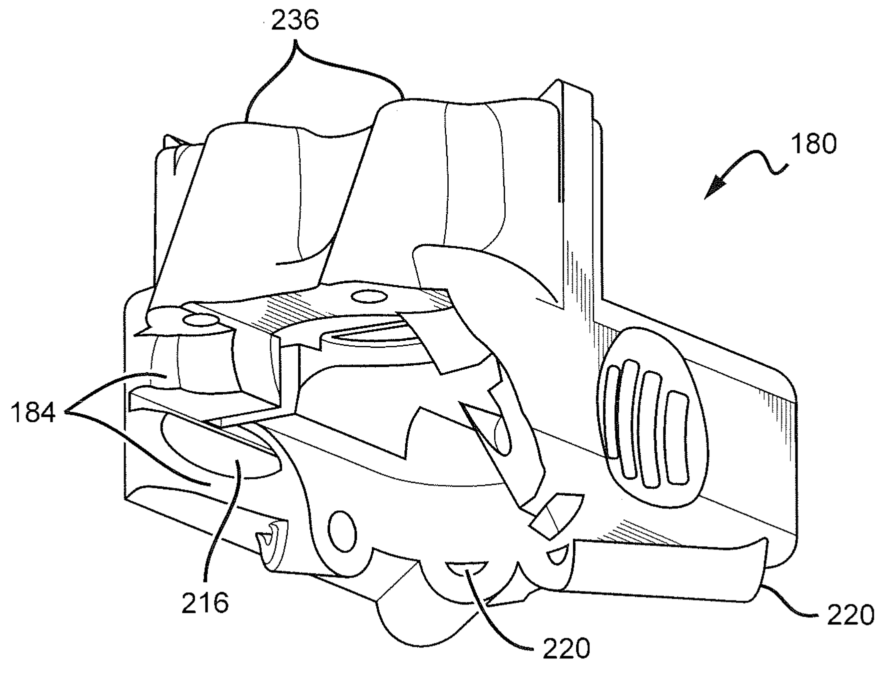
FIG. 13 illustrates an isometric view of a bone contact surface of the patient-specific instrument guide of FIG. 12.

FIGS. 12-13 illustrate an exemplary embodiment of a PSI guide 180 that is configured for guiding precise bone cuts to a talus in the course of performing a total ankle arthroplasty. The PSI guide 180 includes a bone contact surface 184, a horizontal cutting guide 188 having a saw blade slot 192, and a vertical cutting guide 196 having a saw blade slot 200. The PSI guide 180 generally comprises a monolithic body that includes a horizontal guide slot 204 that slidably receives the horizontal cutting guide 188, and includes a vertical guide slot 208 that slidably receives the vertical cutting guide 196. In general, the PSI guide 180 is comprised of a rigid material, such as a 3D printable material, that may be adapted to a specific bone surface of a patient. The cutting guides 188, 196 preferably are comprised of a metal suitable for protecting the PSI guide 180 from a saw blade during bone cutting.

As will be appreciated, the cutting guides 188, 196 may be pulled out of their respective guide slots 192, 208 by a practitioner. The PSI guide 180 includes a front notch 224 disposed above and below the horizontal cutting guide 188 to enable the practitioner to grasp the cutting guide 188 with an index finger and a thumb. Similarly, a top notch 228 is disposed adjacent to both sides of the vertical cutting guide 196 to enable the practitioner to pull the cutting guide 196 out of the guide slot 208. Further, the PSI guide 180 includes a rear notch (not shown) behind each of the cutting guides 188, 196 to enable the practitioner to use a finger or a thumb to push the cutting guides 188, 196 out of the PSI guide 180, as desired.

Figure 14:
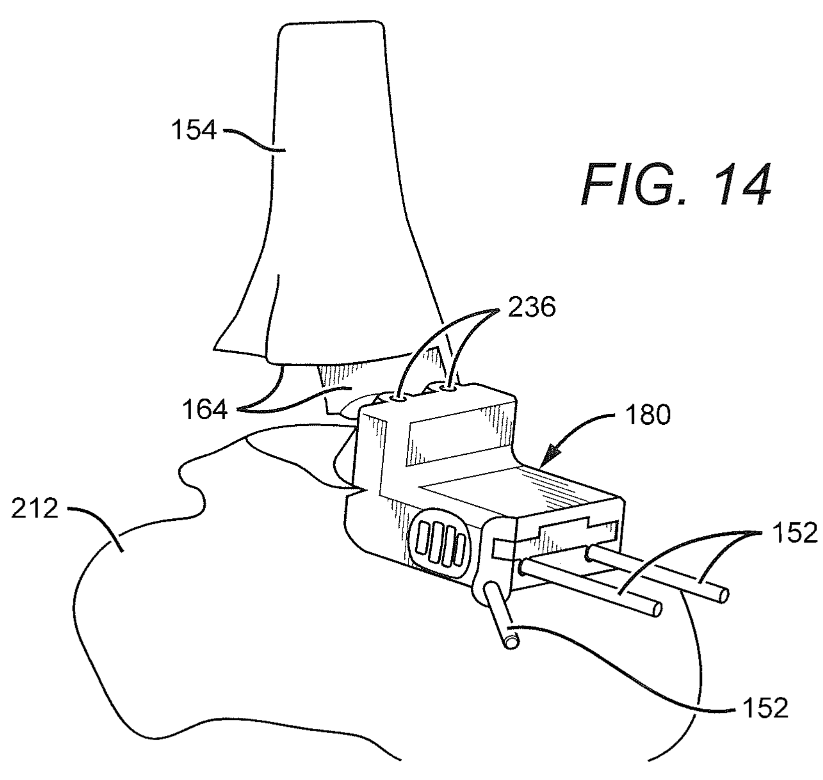
FIG. 14 illustrates the patient-specific instrument guide of FIG. 12 fixated to a talus during a total ankle arthroplasty surgery.
Figure 15:
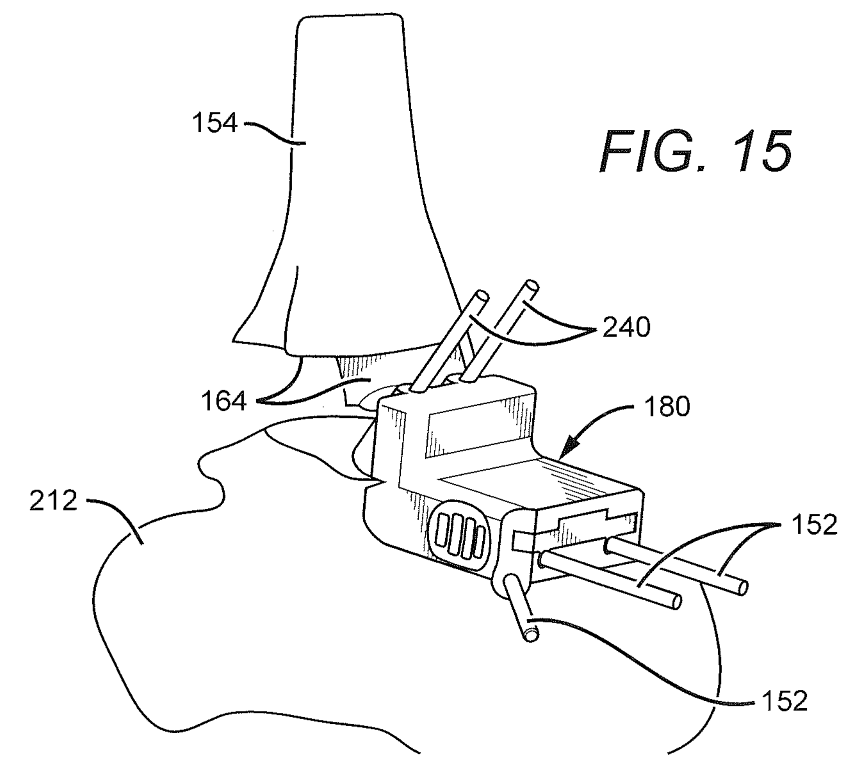
FIG. 15 illustrates the patient-specific instrument guide of FIG. 12 guiding angled positioning pins driven into a talus during a total ankle arthroplasty surgery.

The PSI guide 180 includes several holes to facilitate optimally fixating the PSI guide 180 to a target bone of a patient to be treated, such as a talus 212 shown in FIGS. 14-15. A pair of fixation holes 216 are disposed at the front of the PSI guide 180 and extend through the guide 180 to the bone contact surface 184 shown in FIG. 13. As further shown in FIG. 13, the PSI guide 180 includes at least one angulated fixation hole 220 that extends through the PSI guide 180 at an angle with respect to the fixation holes 216. The fixation holes 216 and the angulated fixation hole 220 are configured to receive fixation pins 152, as shown in FIGS. 14-15. The fixation pins 152 extending through the fixation holes 144 hold the bone contact surface 184 in direct contact with a target bone to be treated, such as the talus 212 shown in FIGS. 14-15. The fixation pin 152 extending through the angulated fixation hole 220 fixates the horizontal cutting guide 188 within the horizontal guide slot 204. In some embodiments, the fixation pin 152 extending through the angulated fixation hole 220 may be configured to further stabilize the bone contact surface 184 against the target bone to be treated.

Figure 17:
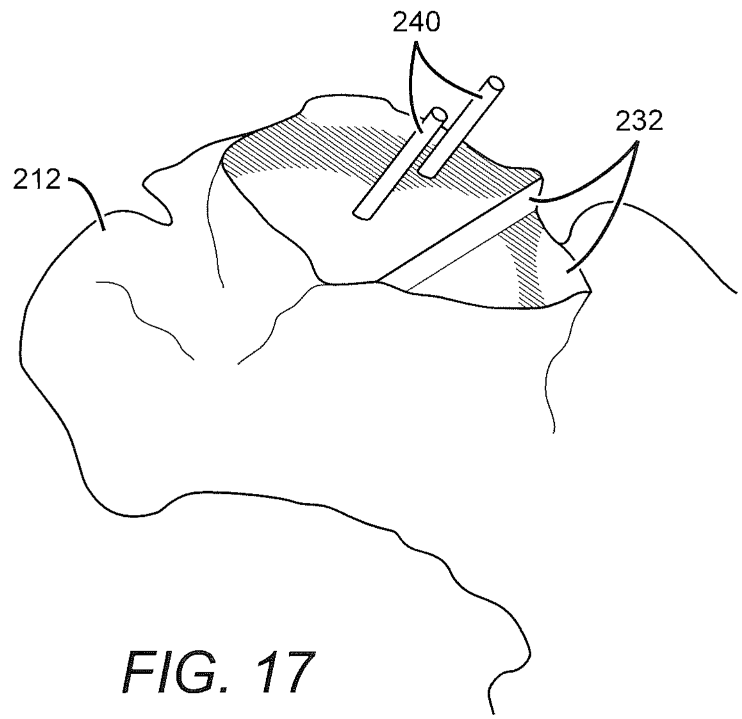
FIG. 17 illustrates the angled positioning pins remaining in the talus after removal of the patient-specific instrument guide.

As described hereinabove in connection with the PSI guide 100, is contemplated that the PSI guide 180 is capable of being adapted to a specific bone surface of a patient, such as the talus 212 shown in FIGS. 14-15. FIG. 13 illustrates an exemplary embodiment of the bone contact surface 184 that is adapted to contact the talus 212 of a patient, as shown in FIGS. 14-15. It is envisioned that the bone contact surface 184 can be adapted to the target bone surface, such as the talus 212, based on medical imaging. Thus, the PSI guide 180 and the bone contact surface 184 may be 3D printed according to the patient's anatomy, allowing for precise positioning of the PSI guide 180 in preparation for performing a precise bone cut. For example, during a total ankle arthroplasty, the PSI guide 180 is placed in optimal contact with the talus 212 as shown in FIG. 14, a saw blade is inserted through the saw blade slots 192, 200, discussed with respect to FIGS. 12-13, and precise bone cuts 232 are formed in the talus 212, as shown in FIG. 17.

Figure 16:
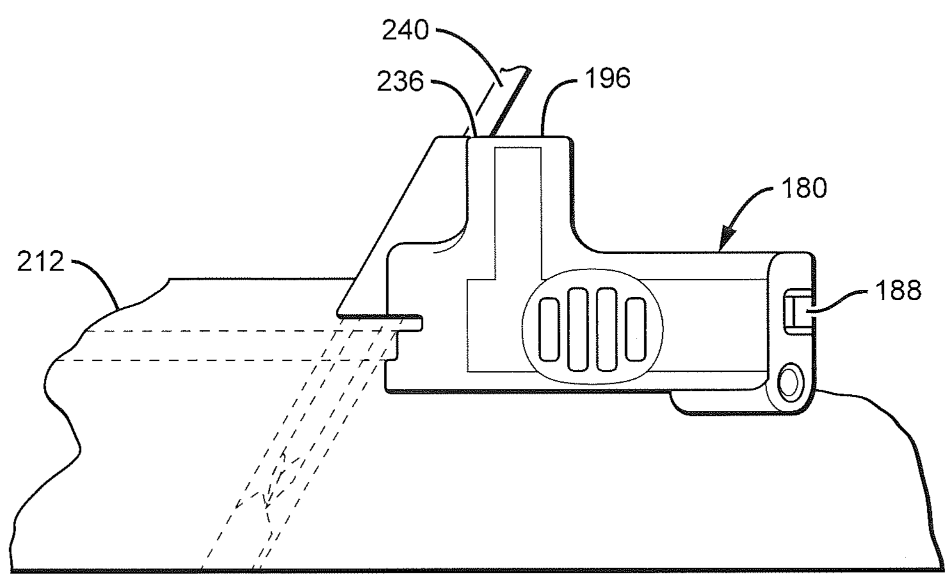
FIG. 16 illustrates the patient-specific instrument guide and angled positioning pins shown in FIG. 15.
Figure 18:
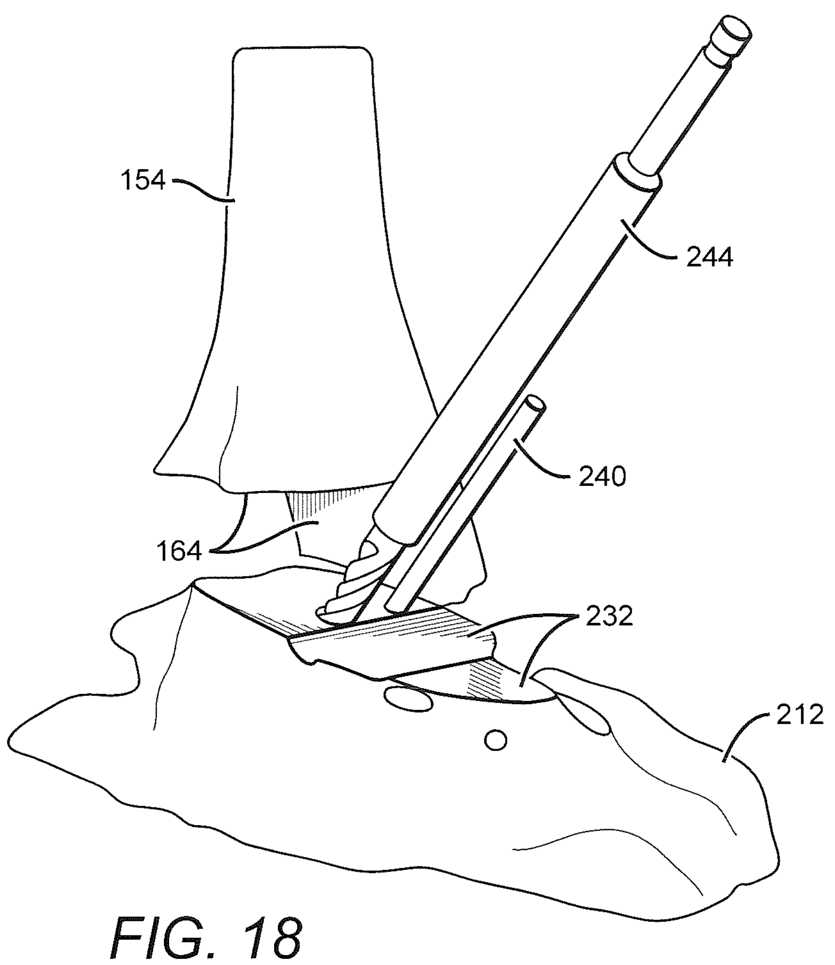
FIG. 18 illustrates a cannulated drill being guided by the angled positioning pins during preparing the talus for a talar implant.
Figure 19:
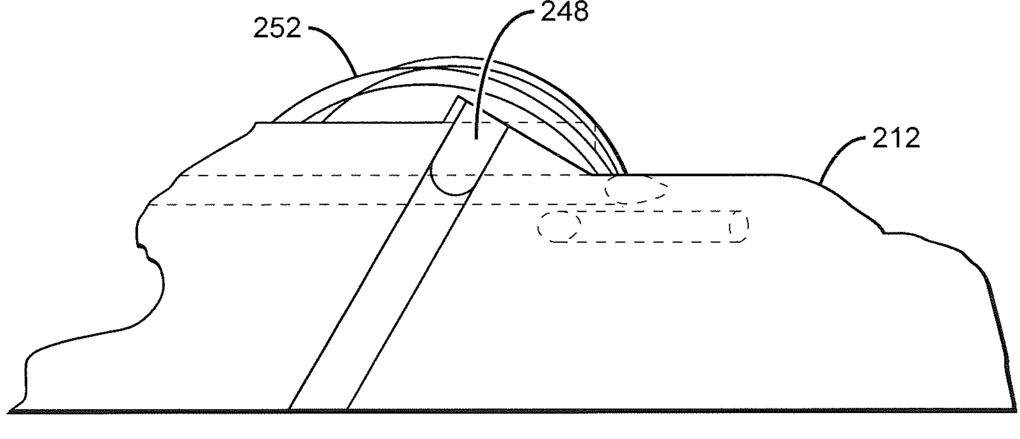
FIG. 19 illustrates a side ghost view of pegs of the talar implant extending into holes drilled in the talus of FIG. 18.

As shown in FIGS. 12-13, the PSI guide 180 includes a pair of angled implant positioning holes 236 that are configured to receive positioning pins 240, as shown in FIGS. 15-16. It is contemplated that the angled implant positioning holes 236 can assist a surgeon with preparing properly angled holes to receive talar pegs 248 protruding from a talar implant 252. In practice, therefore, the PSI guide 180 can be optimally fixated to the talus 212, as shown in FIG. 15, and the positioning pins 240 can be inserted through the positioning holes 236 and driven into the talus 212, as shown in FIGS. 15-16. As shown in FIG. 17, the positioning pins 240 can be left in the talus 212 upon removing the PSI guide 180. Once the PSI guide 180 is removed, the positioning pins 240 are found extending from the talus 212 with an optimal angle and separation distance. It is contemplated that the positioning pins 240 may be used to guide a cannulated drill 244 for the purpose of drilling holes in the talus 212, as shown in FIG. 18. After the desired holes are drilled, the positioning pins 240 may be removed from the talus 212. The talar pegs 248 may then be inserted into the drilled holes when the talar implant 252 is fixated to the talus 212, as shown in FIG. 19.

Figure 20:
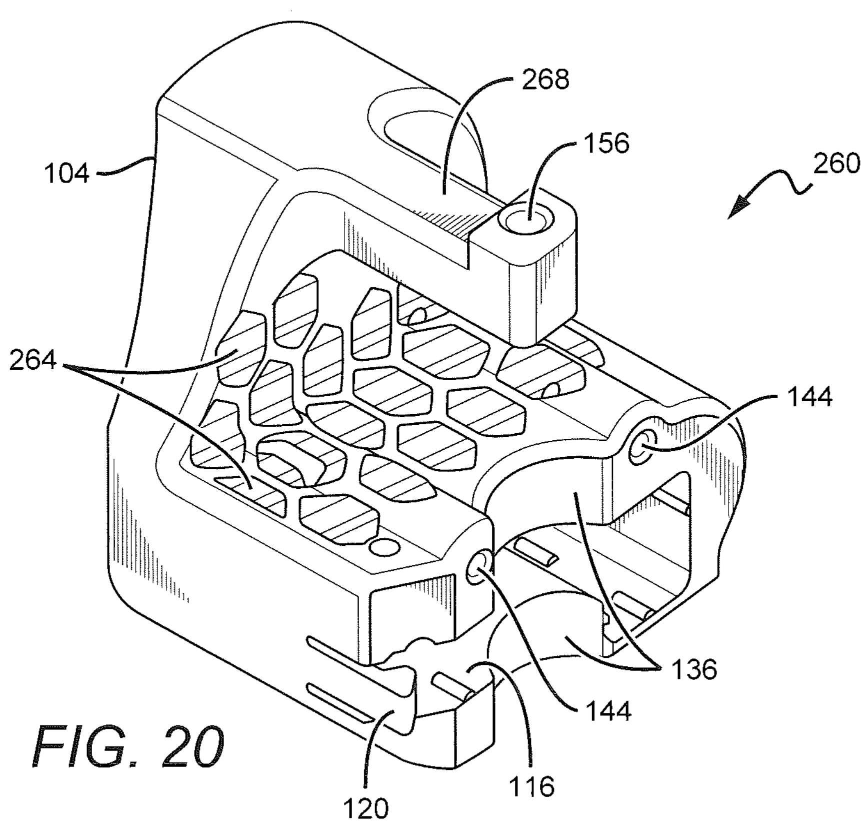
FIG. 20 illustrates a front isometric view of an exemplary embodiment of a patient-specific instrument guide that is configured to guide cuts to a tibia during performing a total ankle arthroplasty surgery.
Figure 21:
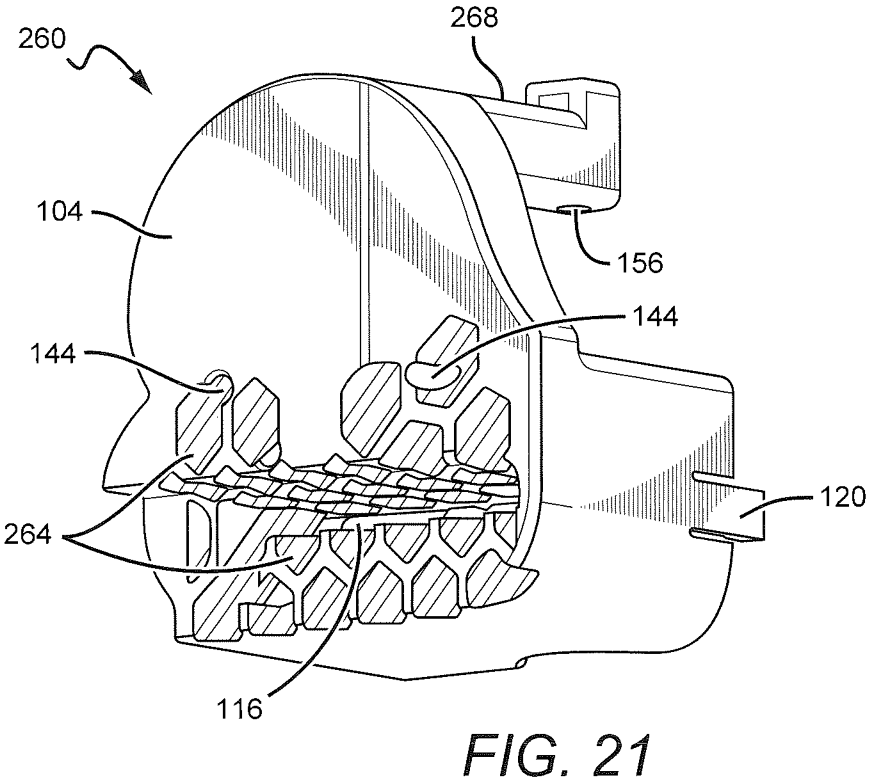
FIG. 21 illustrates a rear isometric view of the patient-specific instrument guide of FIG. 20.
Figure 22:
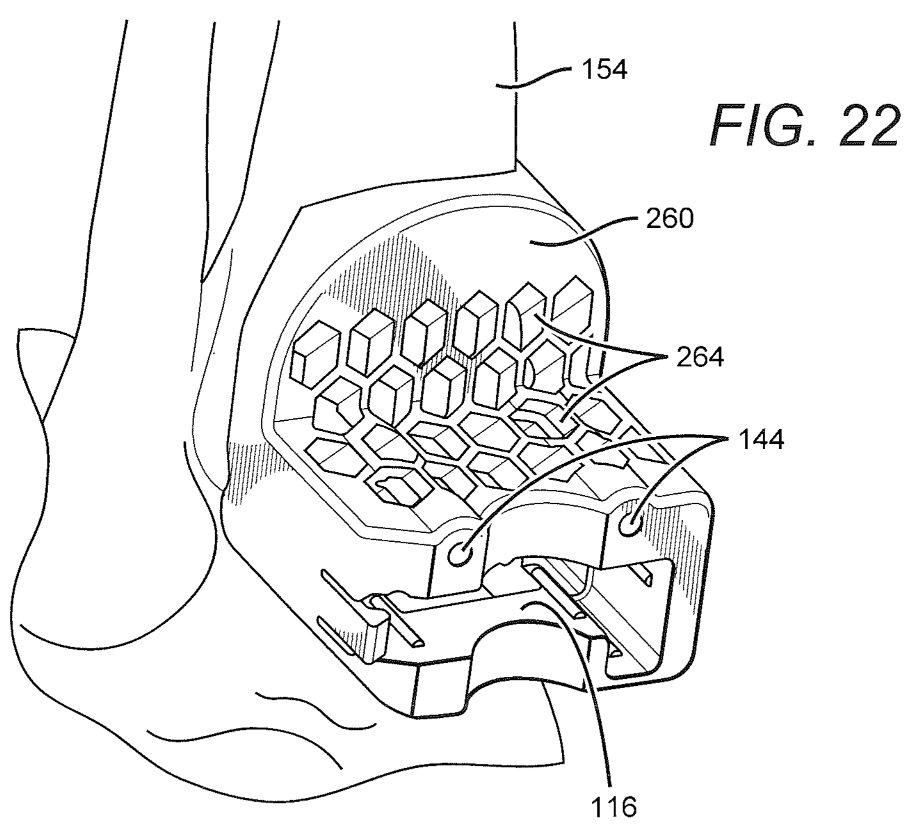
FIG. 22 illustrates an isometric view of the patient-specific instrument guide of FIG. 20 optimally coupled with a tibia.
Figure 23:
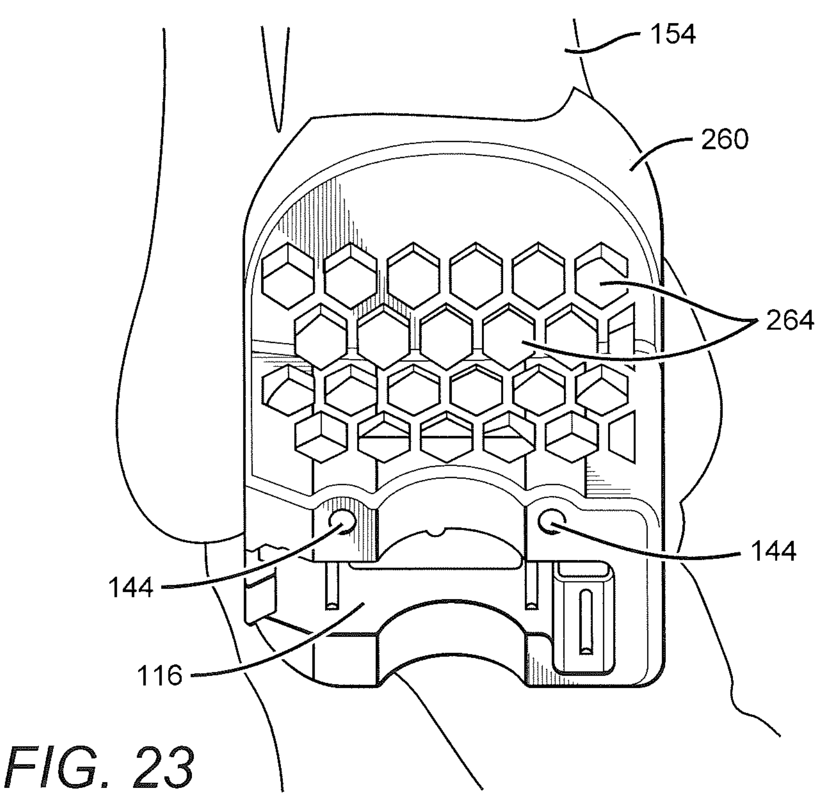
FIG. 23 illustrates the patient-specific instrument guide of FIG. 22 coupled with a tibia, such that the bone surface underneath the patient-specific instrument guide is observable.

FIG. 20-21 illustrate an exemplary embodiment of a PSI guide 260 that is configured for performing total ankle arthroplasty surgeries. The PSI guide 260 is substantially similar to the PSI guide 100, with the exception that the PSI guide 260 comprises a monolithic body that includes a multiplicity of angled holes 264 extending through the body in parallel. The angled holes 264 generally are configured to provide better visibility of the surface of a bone to be treated: For example, when the PSI guide 260 is adapted to contact the tibia 154 of a patient, as shown in FIGS. 22-23, the angled holes 264 provide a relatively unobstructed view of the bone surface underneath the PSI guide 260. As such, the holes 264 preferably are oriented in a direction through the PSI guide 260 that optimizes a surgeon's view of the bone surface and cutting of the bone during surgery.

In the illustrated embodiment of the PSI guide 260, the holes 264 each includes a hexagonal cross-sectional shape, thereby forming a honeycomb arrangement across the PSI guide 260. It is contemplated, however, that the holes 264 may include any cross-sectional shape that is found to improve visibility of the bone surface and cutting of the bone during surgery, as well as imparting a suitable degree of rigidity to the PSI guide 260. For example, the cross-sectional shape of the holes 264 may be any shape that generally tessellates the body of the PSI guide 260, such as circular, ovoid, quadrilateral, triangular, polygonal, rhomboid, trapezoid, and the like. Further, in some embodiments, the multiplicity of holes 264 may include groups of holes having different cross-sectional shapes, without limitation.

Turning again to FIGS. 20-21, the illustrated embodiment of the PSI guide 260 further includes a protruding member 268 that includes a positioning hole 156. The protruding member 268 includes only one positioning hole 156 in lieu of the multiple positioning holes 156 included in the PSI guide 100. The positioning hole 156 shown in FIGS. 20-21 is located on the PSI guide 260 and configured to receive a positioning pins 160, as shown in FIG. 8, to assist the surgeon with optimally positioning the PSI guide 260 in contact with the target bone, such as the tibia 154 shown in FIGS. 22-23. As will be appreciated, the protruding member 268 provides an unobstructed view of the holes 264 while still providing a means for positioning the PSI guide 260 on the target bone.

Figure 24:
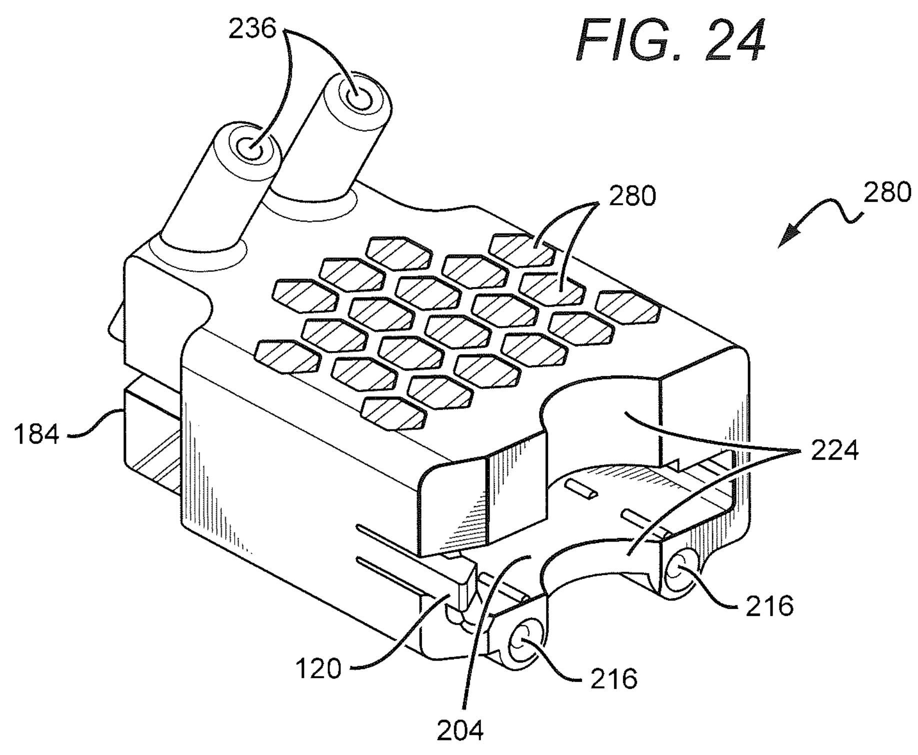
FIG. 24 illustrates an isometric view of an exemplary embodiment of a patient-specific instrument guide that is configured to guide cuts to a talus during performing a total ankle arthroplasty surgery.
Figure 25:
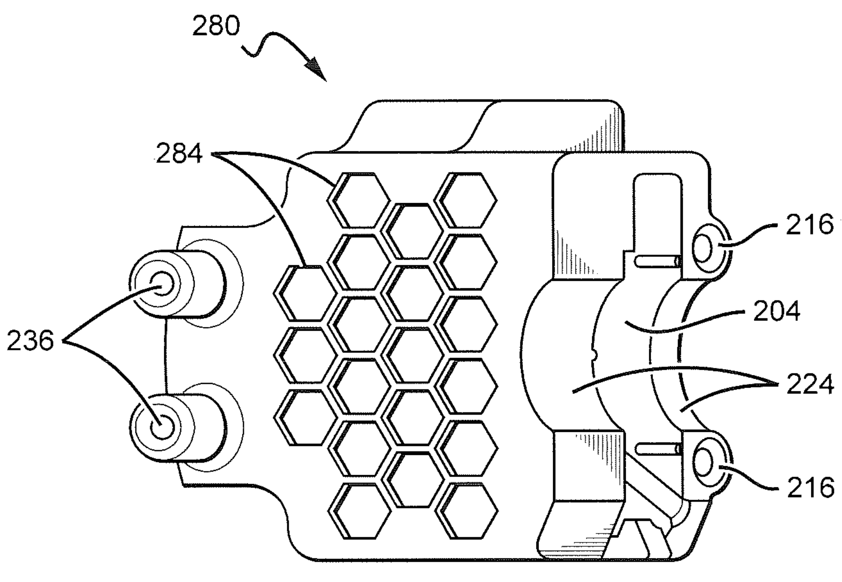
FIG. 25 illustrates a top view of the patient-specific instrument guide of FIG. 24.

FIGS. 24-25 illustrate an exemplary embodiment of a PSI guide 280 that is configured for guiding precise bone cuts to a talus in the course of performing a total ankle arthroplasty. The PSI guide 280 is substantially similar to the PSI guide 180 of FIGS. 12-13, with the exception that the PSI guide 280 includes a multiplicity of angled holes 284 extending through the PSI guide 280 in parallel. The holes 284 are substantially identical to the holes 264 discussed with respect to FIGS. 20-21. As such, the holes 284 are configured to provide a surgeon with a relatively unobstructed view of the bone surface underneath the PSI guide 280. Further, the holes 284 are oriented in a direction through the PSI guide 280 that optimizes the surgeon's view of the bone surface and cutting of the bone during surgery.

Figure 26:
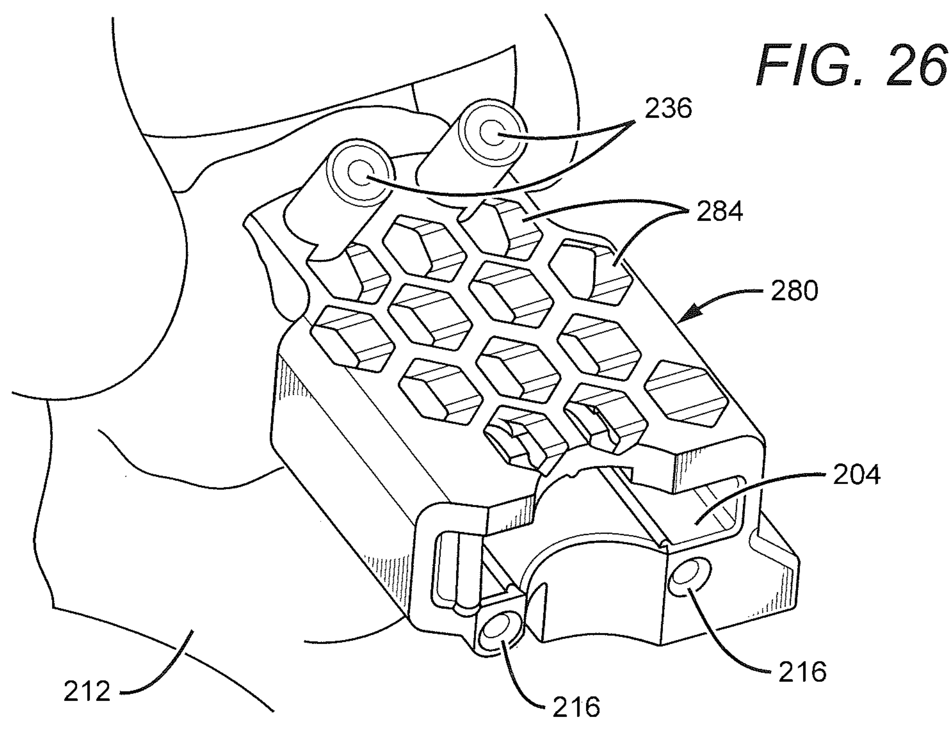
FIG. 26 illustrates an isometric view of the patient-specific instrument guide of FIG. 24 optimally coupled with a talus.
Figure 27:
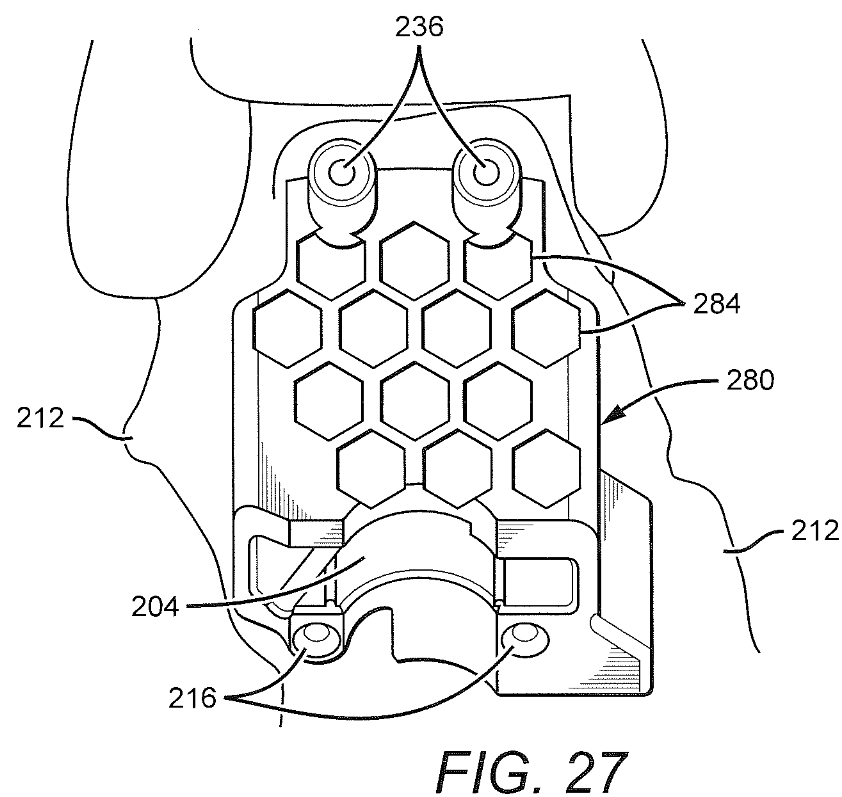
FIG. 27 illustrates the patient-specific instrument guide of FIG. 26 coupled with a talus, such that the bone surface underneath the patient-specific instrument guide is observable.

FIGS. 26-27 illustrate the PSI guide 280 placed into contact with the surface of a talus 212. As best illustrated in FIG. 27, the holes 284 provide a view of the portion of bone directly underneath the PSI guide 280. Although the holes 284 are shown having a hexagonal cross-sectional shape, it is contemplated that the holes 284 may include any cross-sectional shape that improves visibility of the bone surface and cutting of the bone during surgery. In some embodiments, for example, the cross-sectional shape of the holes 284 may be any shape that generally tessellates the body of the PSI guide 280, as well as combinations of different shapes capable of tessellating the body of the PSI guide 280. As such, the shape of the holes 284 may be any of circular, ovoid, quadrilateral, triangular, polygonal, rhomboid, trapezoid, and any of various combinations thereof, without limitation.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. To the extent there are variations of the invention, which are within the spirit of the disclosure or equivalent to the inventions found in the claims, it is the intent that this patent will cover those variations as well. Therefore, the present disclosure is to be understood as not limited by the specific embodiments described herein, but only by scope of the appended claims.

What is claimed is:

1. A patient-specific instrument guide comprising:

a monolithic body comprising a bone contact surface, wherein the bone contact surface is adapted to a target bone surface of a patient using medical imaging;

the body including one or more guide slots that each slidably receives one or more cutting guides, wherein the one or more cutting guides are configured to receive a saw blade, drill or reamer during cutting of the bone and wherein at least one angulated pin slot is positioned on the cutting guide to position the cutting guide within the patient body;

a retaining guide that is disposed adjacent to the guide slots and configured to hold the cutting guide within the guide slot, the retaining guide having at least a distal protrusion;

a pair of fixation holes disposed at the front of the monolithic body and extend through to the bone contact surface;

and wherein one or more positioning holes are disposed along a top of on the body and configured to:

i) receive positioning pins to assist a surgeon with optimally positioning the bone contact surface with the bone; and ii) guide a cannulated drill.

2. The patient-specific instrument guide of claim 1, wherein the one or more cutting guides are comprised of a metal suitable for protecting the body from a saw blade during bone cutting.

3. The patient-specific instrument guide of claim 2, wherein the one or more cutting guides each includes a saw blade slot configured to guide a saw blade during bone cutting.

4. The patient-specific instrument guide of claim 1, wherein the one or more cutting guides comprises a horizontal cutting guide and a vertical cutting guide orientated to guide cutting a talus during a total ankle arthroplasty surgery.

5. The patient-specific instrument guide of claim 1, wherein the one or more cutting guides comprises a horizontal cutting guide oriented to guide cutting a tibia during a total ankle arthroplasty surgery.

6. The patient-specific instrument guide of claim 1, wherein the body is comprised of a 3D printable material.

7. The patient-specific instrument guide of claim 6, wherein the body is configured to be 3D printed according to medical imaging of a patient's anatomy.

8. The patient-specific instrument guide of claim 6, wherein the bone contact surface is configured to optimally contact the surface of a specific bone of the patient.

9. The patient-specific instrument guide of claim 8, wherein the specific bone is a tibia for the purpose of a total ankle arthroplasty surgery.

10. The patient-specific instrument guide of claim 8, wherein the specific bone is a talus for the purpose of a total ankle arthroplasty surgery.

11. The patient-specific instrument guide of claim 1, wherein the one or more fixation holes are configured to received fixation pins to hold the bone contact surface in direct contact with the bone.

12. The patient-specific instrument guide of claim 1, wherein the cutting guide includes at least one angulated pin slot that extends through the cutting guide.

13. The patient-specific instrument guide of claim 12, wherein the at least one angulated pin slot is configured to fixate the cutting guide within the body.

14. The patient-specific instrument guide of claim 1, wherein the body includes one or more angled implant positioning holes that are configured to receive positioning pins.

15. The patient-specific instrument guide of claim 14, wherein the one or more angled implant positioning holes are configured to assist a surgeon with preparing properly angled holes to receive pegs of an implant.

16. The patient-specific instrument guide of claim 15, wherein the one or more angled implant positioning holes are configured to guide a surgeon with driving positioning pins into a bone at an optimal angle and separation distance, the positioning pins being configured to receive a cannulated drill for the purpose of drilling holes in the bone in preparation for coupling the implant to the bone.

17. A patient-specific instrument guide comprising: a body comprising a bone contact surface configured to contact a bone surface of a patient, wherein the body includes a multiplicity of angled holes extending through the body in parallel so as to provide visibility of the bone surface underneath the body so as to optimize a surgeon's view of the bone surface during cutting of the bone.

18. The patient-specific instrument guide of claim 17, wherein each of the multiplicity of angled holes comprises a cross-sectional shape capable of tessellating the surface of the body.

* * * * *